(12) United States Patent
O'brien et al.

(10) Patent No.: US 11,558,178 B2
(45) Date of Patent: Jan. 17, 2023

(54) SYSTEM AND METHOD FOR PRESCRIPTION SECURITY AND AUTHENTICATION

(71) Applicant: Walmart Apollo, LLC, Bentonville, AR (US)

(72) Inventors: John J. O'brien, Farmington, AR (US); David M. Nelms, Rogers, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 1006 days.

(21) Appl. No.: 16/262,671

(22) Filed: Jan. 30, 2019

(65) Prior Publication Data
US 2019/0237176 A1 Aug. 1, 2019

Related U.S. Application Data

(60) Provisional application No. 62/624,711, filed on Jan. 31, 2018.

(51) Int. Cl.
| | |
|---|---|
| H04L 29/06 | (2006.01) |
| H04L 9/06 | (2006.01) |
| G16H 20/10 | (2018.01) |
| G06Q 20/06 | (2012.01) |
| B64C 39/02 | (2006.01) |
| H04L 9/00 | (2022.01) |
| G07F 17/00 | (2006.01) |
| G16H 10/00 | (2018.01) |

(52) U.S. Cl.
CPC .......... *H04L 9/0637* (2013.01); *B64C 39/024* (2013.01); *G06Q 20/065* (2013.01); *G07F 17/0092* (2013.01); *G16H 10/00* (2018.01); *G16H 20/10* (2018.01); *H04L 9/006* (2013.01); *H04L 9/0643* (2013.01); *B64C 2201/128* (2013.01); *H04L 9/50* (2022.05)

(58) Field of Classification Search
None
See application file for complete search history.

(56) References Cited

U.S. PATENT DOCUMENTS

| | | |
|---|---|---|
| 6,882,269 B2 | 4/2005 | Moreno |
| 7,848,934 B2 | 12/2010 | Kobylevsky et al. |
| (Continued) | | |

FOREIGN PATENT DOCUMENTS

RU 2695509 C1 * 7/2019 ........... G06Q 20/065

OTHER PUBLICATIONS

Jindal, "Blockchain Tech Holds the Answer for the Prescription Drug Crisis", NewsBTC, Jan. 7, 2018, pp. 1-3.
(Continued)

*Primary Examiner* — Andrew J Steinle
(74) *Attorney, Agent, or Firm* — Morgan, Lewis & Bockius LLP; Manita Rawat

(57) ABSTRACT

Systems, methods, and computer-readable storage media for receiving, from an issuer, an electronic prescription for a patient, then fulfilling that prescription using a blockchain/ distributed ledger verification system. The system receives multiple public keys, combines them, then performs a hash function (or other encryption) on that combination. The resulting output is then transmitted to a pharmacy for prescription fulfillment.

20 Claims, 14 Drawing Sheets

(56) References Cited

U.S. PATENT DOCUMENTS

| | | | |
|---|---|---|---|
| 2011/0112970 A1* | 5/2011 | Yu | G06Q 40/00 |
| | | | 705/2 |
| 2011/0153362 A1 | 6/2011 | Valin et al. | |
| 2012/0023193 A1 | 1/2012 | Eisner et al. | |
| 2014/0303989 A1 | 10/2014 | Ferguson | |
| 2015/0236856 A1* | 8/2015 | Moore | H04L 9/3247 |
| | | | 713/176 |
| 2015/0332283 A1 | 11/2015 | Witchey | |
| 2016/0028552 A1 | 1/2016 | Spanos et al. | |
| 2016/0072800 A1 | 3/2016 | Soon-Shiong et al. | |
| 2016/0085938 A1 | 3/2016 | Hans | |
| 2016/0162660 A1 | 6/2016 | Strong | |
| 2017/0132393 A1* | 5/2017 | Natarajan | G06Q 10/087 |

OTHER PUBLICATIONS

International Search Report and Written Opinion dated Mar. 29, 2019, issued in corresponding PCT Application No. PCT/US2019/015843.

* cited by examiner

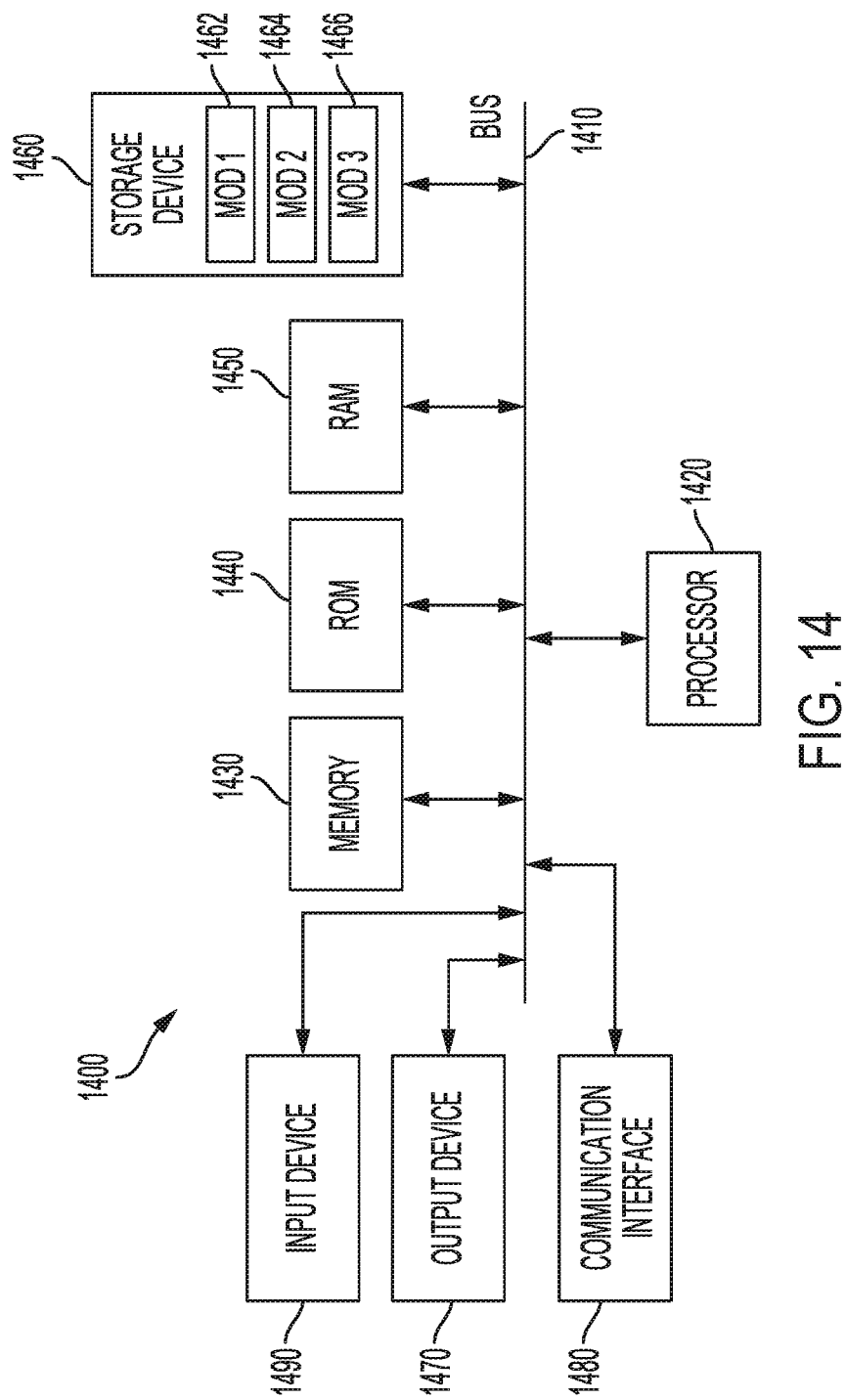

SYSTEM AND METHOD FOR PRESCRIPTION SECURITY AND AUTHENTICATION

PRIORITY APPLICATIONS

This application claims priority to U.S. Patent Application No. 62/624,711, filed Jan. 31, 2018, the entirety of which is incorporated by reference herein.

BACKGROUND

1. Technical Field

The present disclosure relates to an electronic prescription system, and more specifically to a system for authenticating prescriptions and their deliveries using a distributed ledger.

2. Introduction

Electronic prescription systems allow doctors or other medical personal to send prescriptions for restricted medicines to pharmacies, where pharmacists can prepare the medicine and distribute it to customers. This allows physicians and other medical practitioners to transmit an electronic prescription to a pharmacy directly from the point of care. Such systems can improve accuracy, enhance the safety of the patient, and reduce forgery because there is no handwriting for the pharmacist to interpret, nor are there phone calls which may be misheard.

However, forgery and theft of pharmaceuticals are still continuing problems, most prominently for recurring prescriptions and opioids. While current laws and systems require patients picking up a prescription to present a valid identification, additional changes to the system which can provide improved security and reduced theft may (1) improve the accuracy of pharmaceutical distribution and (2) reduce pharmaceutical abuse.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

An example method per this disclosure can include: receiving, from a medical professional, an electronic prescription for a patient; receiving a first public key associated with the medical professional, the first public key: being associated with a blockchain; forming a first alphanumeric code; and being formed via a first algorithmic transformation, executed using a first private key associated with the medical professional, of: an identification of the medical professional; contact information of the medical professional; and an identification of a restricted pharmaceutical associated with the electronic prescription; receiving a second public key associated with the patient, the second public key: being associated with the blockchain; forming a second alphanumeric code; and being formed via a second algorithmic transformation, executed using a second private key associated with the patient, of: an identification of the patient; contact information of the patient; and the identification of the restricted pharmaceutical associated with the electronic prescription; combining, via a processor, the first public key and the second public key sequentially, to form a combined public key; executing, via the processor, a hash function on the combined public key; and transmitting the combined public key to a pharmacy.

An example system as configured described herein can include: a processor; and a computer-readable storage medium having instructions stored which, when executed by the processor, cause the processor to perform operations comprising: receiving, from a medical professional, an electronic prescription for a patient; receiving a first public key associated with the medical professional, the first public key: being associated with a blockchain; forming a first alphanumeric code; and being formed via a first algorithmic transformation, executed using a first private key associated with the medical professional, of: an identification of the medical professional; contact information of the medical professional; and an identification of a restricted pharmaceutical associated with the electronic prescription; receiving a second public key associated with the patient, the second public key: being associated with the blockchain; forming a second alphanumeric code; and being formed via a second algorithmic transformation, executed using a second private key associated with the patient, of: an identification of the patient; contact information of the patient; and the identification of the restricted pharmaceutical associated with the electronic prescription; combining the first public key and the second public key sequentially, to form a combined public key; executing a hash function on the combined public key; and transmitting the combined public key to a pharmacy.

An example non-transitory computer-readable storage medium configured as described herein can store instructions which, when executed on a computing device, cause the computing device to perform operations including: receiving, from a medical professional, an electronic prescription for a patient; receiving a first public key associated with the medical professional, the first public key: being associated with a blockchain; forming a first alphanumeric code; and being formed via a first algorithmic transformation, executed using a first private key associated with the medical professional, of: an identification of the medical professional; contact information of the medical professional; and an identification of a restricted pharmaceutical associated with the electronic prescription; receiving a second public key associated with the patient, the second public key: being associated with the blockchain; forming a second alphanumeric code; and being formed via a second algorithmic transformation, executed using a second private key associated with the patient, of: an identification of the patient; contact information of the patient; and the identification of the restricted pharmaceutical associated with the electronic prescription; combining the first public key and the second public key sequentially, to form a combined public key; executing a hash function on the combined public key; and transmitting the combined public key to a pharmacy.

BRIEF DESCRIPTION OF THE DRAWINGS

FIG. 14 illustrates an exemplary computer system.

DETAILED DESCRIPTION

Various embodiments of the disclosure are described in detail below. While specific implementations are described, it should be understood that this is done for illustration purposes only. Other components and configurations may be used without parting from the spirit and scope of the disclosure.

Systems and methods in accordance with some embodiments provide for a combined delivery of medication prescriptions and groceries or other items of interest to a desired location.

Figure 1:
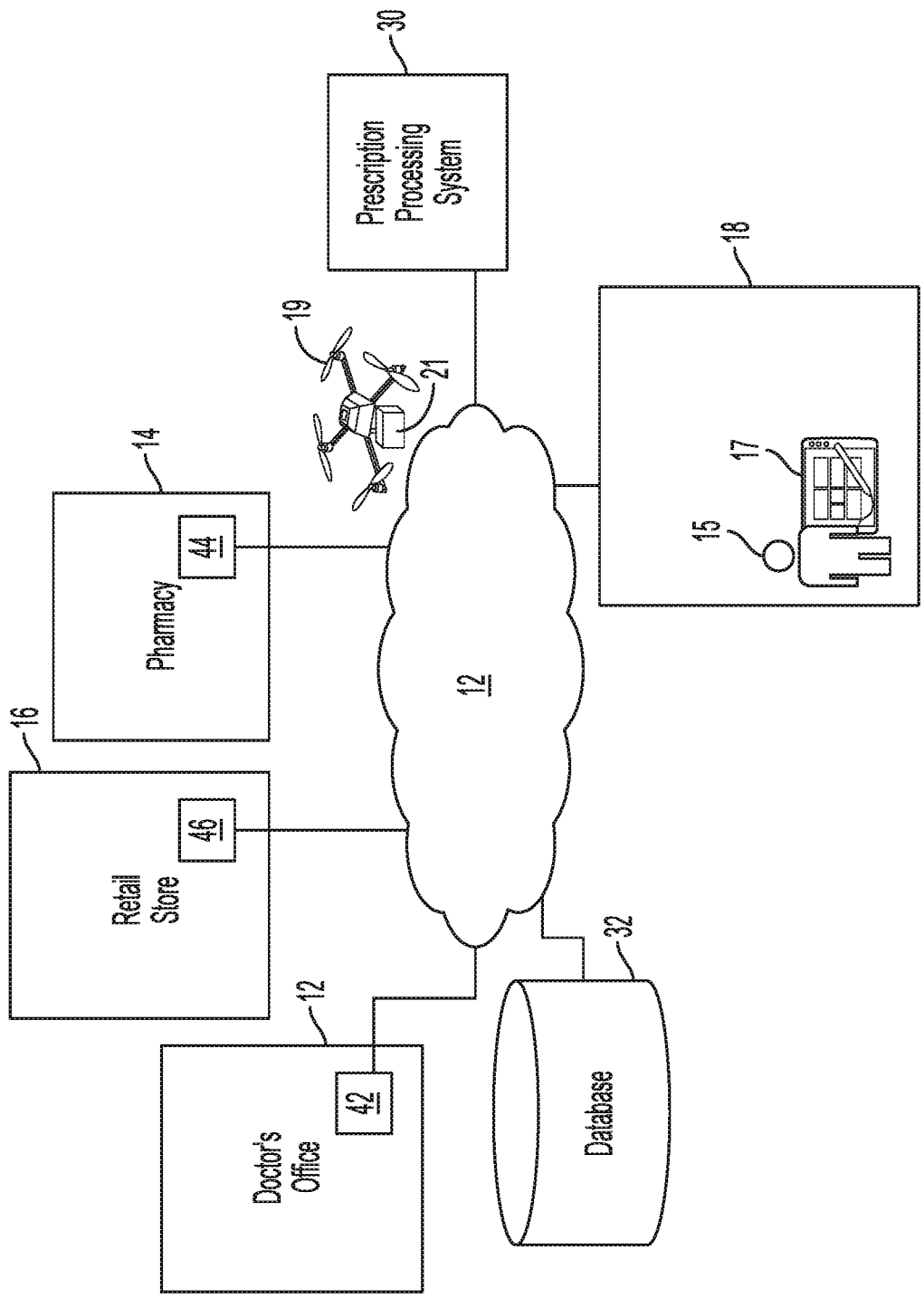
FIG. 1 illustrates an exemplary environment in which embodiments may be practiced.

FIG. 1 is a diagram of an environment in which embodiments may be practiced. The environment may include entities involved in the delivery of pharmacy items and groceries or other retail items, in accordance with some embodiments. Entities may include but not be limited to a doctor's office 12, pharmacy 14, grocery store 16, and user location 18 such as a home or office. The environment may include an autonomous vehicle 19 such as a driverless, self-driving, or robotic vehicle, unmanned aerial vehicle (UAV), or the like, which can deliver the pharmacy items and groceries or other retail items between the various entities. In other embodiments, pharmacy items and groceries or other retail items are delivered by conventional vehicles, e.g., automobiles, trucks, and so on. In some embodiments, the information required for delivering a prescription may be transmitted and authenticated through a peer-peer ledger system, which will allow the autonomous vehicle to receive pickup information and where to deliver the prescription to; as well as authentication for the vehicle and authentication of the customer when receiving the package.

Each of the doctor's office 12, pharmacy 14, grocery store 16, and user location 18 may include at least one computer processor 17, 42, 44, 46 and network interface for communicating with each other and/or other electronic devices such as a prescription processing system 30 and database 32 via a network 12. The network 12 may be a public switched telephone network (PSTN), a mobile communications network, a data network, such as a local area network (LAN) or wide area network (WAN), or a combination thereof, or other communication network known to those of ordinary skill in the art.

A consumer 15 may visit the doctor's office 12, or a hospital, medical center, or other location where the consumer 15 may receive a prescription. For purposes of explanation, a consumer 15 may also be referred to as a medication recipient or recipient when the consumer 15 is intended to be the recipient of prescribed medication. The consumer 15 may then visit the pharmacy 14 to receive the medication identified in the prescription. The consumer 15 may subsequently visit a retail establishment 16 such as a grocery store to purchase other items of interest, which may or may not relate to the medication acquired at the pharmacy 14. In some embodiments, these items may be purchased that the pharmacy 14 instead of a physically different store. In some embodiments, the consumer 15 may fill a prescription online, and also purchase the other items online, for example, at a same or different websites.

The prescription processing system 30 provides for the delivery of a medication prescription to a desired receiving location 18 of a recipient 15 such as a home, and identifies other items such as groceries, supplies, or other retail items that can be bundled and delivered with the medication prescription to the desired receiving location 18. In the foregoing example, a consumer 15 visiting the pharmacy 14 and/or store 16 may desire to ship the medication and other items under a same shipment, for example, in instances where the medication is not available at the time of the request made by the consumer 15 at the pharmacy 14. In other embodiments, the consumer 15 may order the medication online using a smartphone or other computer, for example, refills, along with other items, whereby the medication and items can be bundled and shipped together to a location of preference.

The prescription processing system 30 may offer additional features such as automatic replenishment of a prescription and/or purchase recommendations based on prescription information, generating alerts sent to the pharmacy 14 when inventory supplies fall below a predetermined threshold, cross-selling, monitoring, advertising, notifications, and other related features. Alerts can be sent from the peer-peer ledger system, which is communicated to the person's smart device.

Figure 2:
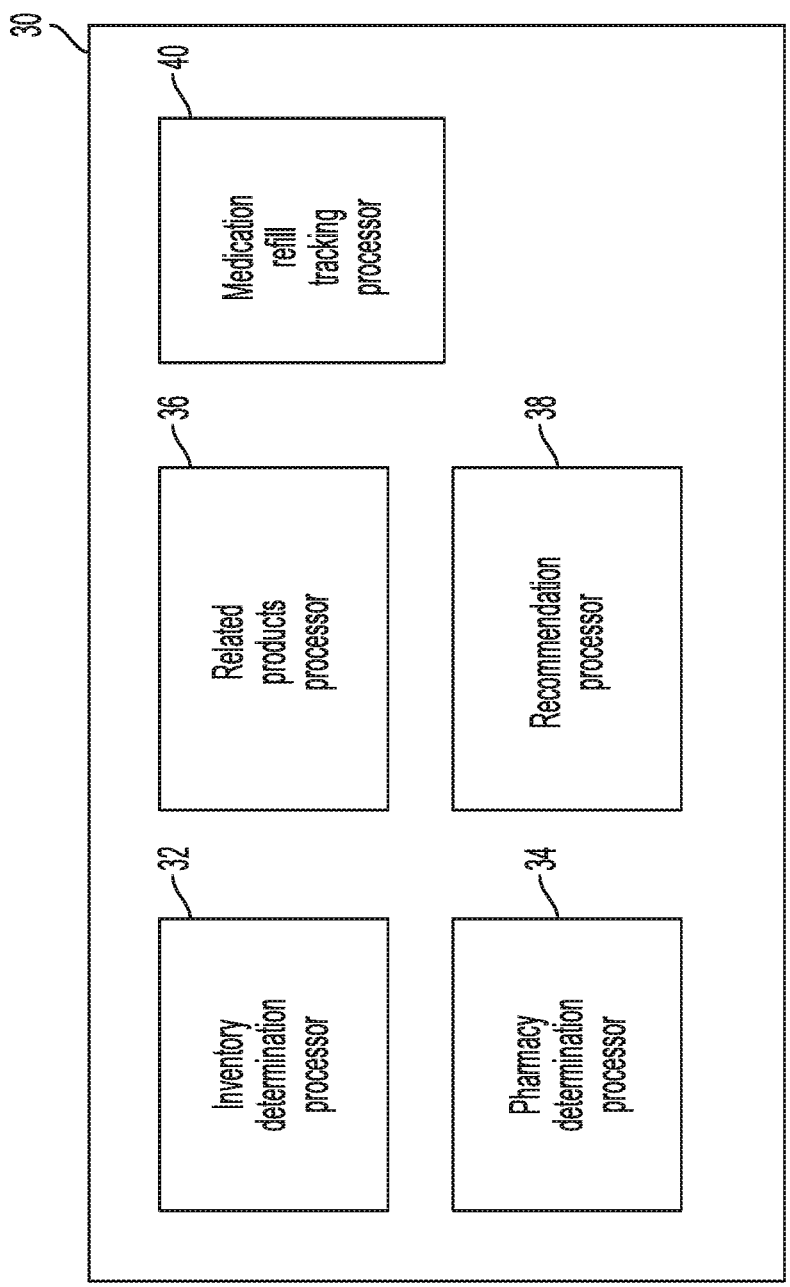
FIG. 2 illustrates an exemplary prescription processing system, in accordance with some embodiments.

FIG. 2 is a block diagram of a prescription processing system 30, in accordance with some embodiments. The prescription processing system 30 can be implemented in the environment illustrated and described with respect to FIG. 1.

The prescription processing system 30 may include an inventory determination processor 32, a pharmacy determination processor 34, a related products generator 36, a product recommendation processor 38, and a medication refill tracking processor 40. Some or all of these elements of the prescription processing system 30 may be present under a same computer hardware platform. In other embodiments, these elements may be located on two or more different computer hardware platform, and can communicate with each other and/or other elements of the prescription processing system 30 via the communication network 12, for example, wired or wireless network that exchanges data electronically.

The inventory determination processor 32 keeps track of medication availability. In doing so, the inventory determination processor 32 may receive a communication from a pharmacy processor 44 when a consumer's medication prescription is processed, whereby a predetermined amount of medication is allotted to the consumer recipient 15. For example, a consumer 15 may receive a prescription from a doctor. In doing so, the order is entered into the doctor office processor 42 and submitted to the pharmacy 14. The inventory determination processor 32 may receive this information from the doctor's processor 42 and/or the pharmacy processor 44. The inventory determination processor 32 can establish from this information an amount of available medication at the pharmacy 14. The inventory determination processor 32 can check for the availability of inventory. Here, the consumer 15 can access the program, for example, by opt into the program. The doctor office processor 42 may process the prescription information, then send the prescription information to the pharmacy processor 44 along with customer information.

The prescription processing system 30 may include one or more processors for performing blockchain-related processing, and may further include a communication device that is linked to a peer-to-peer network, with affiliated keys for patient, doctor, and pharmacy distributed to a peer-to-peer network, which further communicates this information to the various entities. At each transmission of communication a new block may be formed with the subsequent blocks; which also includes handling, procurement, issuing, or acceptance of the prescription. Prescriptions and their related ingredients, products and their related inventory, retailer and their related inventory, and pharmacy and their related inventory, will share their inventory statuses with the application or the blockchain structure, as blocks of information to the peer-to-peer ledger system, or as inventory statuses with the application.

The doctor office processor 42 and/or other business entity computer device affiliated with the doctor may provide an authentication or other security technique including public and/or private keys when submitted prescriptions in the form of electronic data to other entities, such as the pharmacy 14. Here, the consumer 15, e.g., a patient of the doctor, may also having a public and/or private key for communicating with the consumer's computer device and the doctor office processor 42 and/or other business entity computer device. When the prescription is sent from the doctor office processor 42 or their affiliation to the pharmacy 14 it may include a converged blockchain structure of both the doctor's private/public key and the patient's private/public key. This information will be shared on a peer-to-peer network, where the pharmacy 14 has access to the data, provided the pharmacy's key has been granted access to the prescription.

After the pharmacy processor 44 has authenticated and decrypted the prescription chain, a receiver for example at the pharmacy 14 may view and produce the prescription, which will further alter the blockchain to include but not be limited to the information from the pharmacy, pharmacist, date, time, prescription instructions, dosage instructions, special instructions, handlings, pickup information, authentication, class of drug, or a combination thereof.

Products and services available at the retailer may also have unique blockchain identifiers, which may be aligned with or otherwise related to prescriptions for relevant combination purchasing, which may be contained and referenced from a database.

Through the application or through a peer-to-peer ledger system, referral products will be submitted to the customer, where the customer can opt-in or opt-out of referral purchases.

The system 30 may also alert the consumer 15, e.g., a patient of the doctor, of which pharmacy the consumer 15 will receive the order. The inventory determination processor 32 in coordination with the refill tracking processor 40 can monitor prescription information, such as refill dates and so on. Refill dates are a part of the pharmacy information sent to the pharmacy 14. The purpose of refill dates is to enable to pharmacy 14 to better predict the need of pharmaceuticals. In some embodiments, refills are accomplished through blockchain data that contains information on refill dates, etc. Alerts may be parsed when refill dates have been achieved from the ledger system to the person's chosen device or method.

The pharmacy determination processor 34 can identify a plurality of pharmacies may be available for prescribing a medication. The pharmacy determination processor 34 can compare a current location of the recipient 15, for example, by GPS communicating with the recipient's smartphone 17, to the location of different pharmacies, and provide the result to the pharmacy determination processor 34, which can recommend the closest pharmacy, or other parameter, for example, the largest pharmacy, the pharmacy where the consumer 15 has previous relationship, the pharmacy having other goods of interest such as food that can be bundled with the medication. Pharmacy providers may have their information stored on a peer-peer ledger system. Thus, when a prescription has been sent by a doctor to the patient's record, the patient will have options to view and select pharmacies. Once selected, the prescription will be transmitted to the chosen pharmacy.

The identification of a pharmacy location based on proximity can be determined through the patient and/or pharmacy blockchain profile, which will include information on the geolocation relating to their position. Further, information relating to the expected time of completion of a prescription may also be included. Each of the above may be produced and distributed through the application and its databases, or through the blockchain and a peer-to-peer ledger system. In doing so, the prescription processing system 30 may include a blockchain processor for exchanging delivery information with one or more supply chain entities, wherein the blockchain processor is part of or in communication with a ledger system for communicating with one or more electronic devices of a customer, doctor, pharmacy, courier, and supply chain entities. In other embodiments, blockchain processing is performed external to the prescription processing system 30 or in combination with the blockchain processor of the prescription processing system 30.

The related products processor 36 determines items that may be combined with prescribed medicine so that the prescribed medication and items can be shopped together under a same shipping order to the consumer 15. An association may be established. For example, a prescription has directions, which both the doctor's office computer 42 and the pharmacy computer 44 may store and process. Directions may include a request for the recipient to take with water, milk, juice, or without certain products. The system 30 uses this information to create recommended products to the consumer 15. The consumer 15 can customize the groceries or other items that the consumer 15 desires to receive along with the prescription. The related products processor 36 may receive a shopping list from the shopper 15, i.e., provided electronically from a smartphone 17 or other electronic device.

Couriers, delivery agents, and delivery providers, or the like may distribute information relating to their location, service, availability, and estimated time of completion, with the application. Couriers, delivery agents, and delivery providers, or the like may distribute information relating to their location, service, availability, and estimated time of completion, with the blockchain peer-peer system. To perform a blockchain method in accordance with some embodiments, this will require blockchain private and public keys issues to couriers, delivery agents, delivery providers, or the like.

The recommendation processor 38 compiles data related to buying habits of the consumer 15 and compares this data to the medication prescription to generate recommended buying options. In addition, the recommendation processor 38 can notify the recipient 15 of products being bought that will complement the medication, or conflict with the medication, so that the recipient 15 may select, for example, from a computer user interface, items of interest which may be bundled with the prescribed medication. For example, the recommendation processor 38 can recommend products that may benefit the health of the consumer 15, for example, low sodium foods that may be consumed for the consumer taking cholesterol medication, or sugar free alternative items for consumers taking diabetes medication.

The recommendation processor 38 may also send an alert to the pharmacy processor 44 when a determination is made by the inventory determination processor 32. In some embodiments, refill levels are estimated by the inventory determination processor 32 based upon the purchase date, prescribed dosage per day, quantity in the bottle, or other related information. For example, a 30 day supply starting on the beginning of the month with 1 a day dosage and having 30 pills would indicate the customer would run out by the end of the month.

In some embodiments, alerts are determined from the block of information relating to a prescription, which is provided by the doctor or their affiliates, or the pharmacy. In some embodiments, alerts include time-based, having incremental windows approaching the expiration or replenishment of a prescription. Alerts may be threshold-based on the level of prescription inventory found in a connected device, such as IoT; where further thresholds determine when a product should warrant an alert to the customer. Alerts may provide autonomous reordering or fulfillment of prescription drugs. Alerts may be issued after a product has depleted. Alerts may be shared through the application of this system or distributed through the peer-to-peer ledger system used with a blockchain.

Figure 3:
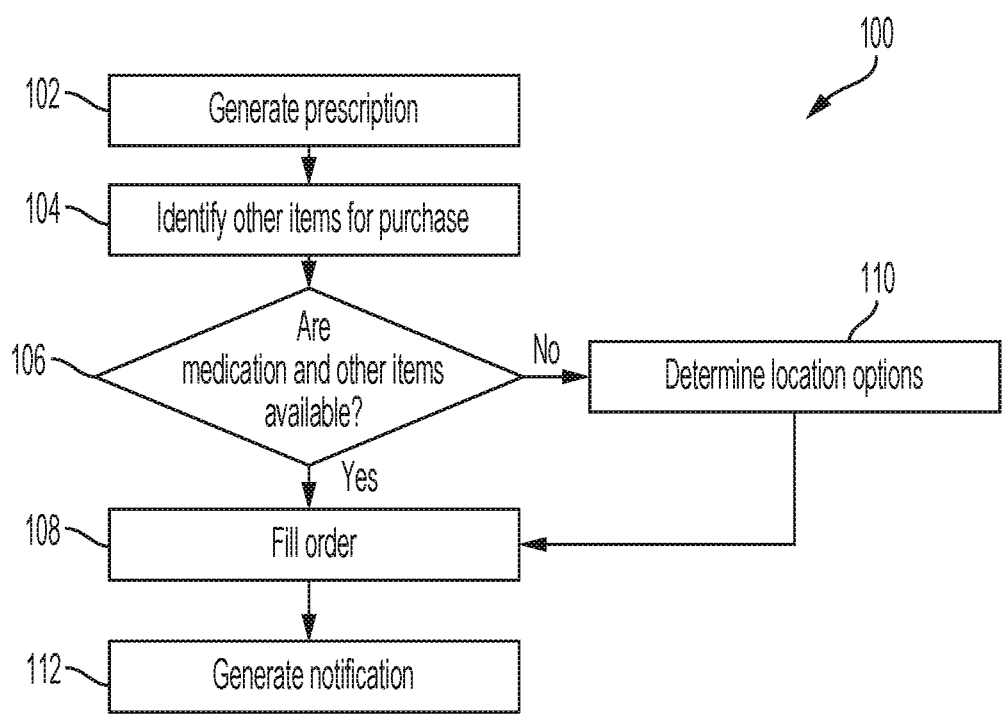
FIG. 3 illustrates an exemplary flowchart of a method for delivering a prescribed medication to a consumer's home, in accordance with some embodiments.

FIG. 3 is a flowchart of a method 100 for delivering a prescribed medication to a consumer's home, in accordance with some embodiments. Some or all of the method 100 can be performed at the prescription processing system 30 of FIGS. 1 and 2, and/or other elements of the environment illustrated in FIG. 1. The method 100 can be governed by instructions that are stored in a memory device of the prescription processing system 30 of FIGS. 1 and 2, and/or other elements of the environment illustrated in FIG. 1, and executed by a hardware processor of the prescription processing system 30 of FIGS. 1 and 2, and/or other elements of the environment illustrated in FIG. 1.

At block 102, a prescription is generated, for example, by a doctor, pharmacist, or other authorized party. The prescription can be filled at a pharmacy, hospital, medical center, or the like. The prescription can be presented at the pharmacy 14 by the medication recipient 15 who receives the prescription at the doctor's office 12, or the prescription can be electronically delivered from the doctor's office computer 42 to the pharmacy computer 44.

At block 104, the prescription recipient 15 identifies additional items for purchase contemporaneously with the filling of the prescription. The prescription recipient 15 may desire to purchase groceries or other products that are related to the prescribed medication, or otherwise purchased for other reasons, for example, convenience on the part of the recipient 15. The sequential order may vary. For example, the items may be purchased before the prescription is filled, or vice versa as shown.

At decision diamond 106, a determination is made whether there is sufficient inventory at the pharmacy 14 at which the request for prescription filling is made. Similarly a determination is made whether the item of interest is available at the store 16 visited by the consumer 15. In some embodiments where the purchase is made online, for example, an e-commerce purchase, a determination is made whether the order can be fulfilled online, for example, by the website at which the order is made. Orders made online may be fulfilled at multiple locations due to one store not having the product and the order being transferred and consolidated at one location to further the capability to deliver products efficiently.

If either the prescription or the other items of interest are not available at their respective locations of initial purchase, at block 110, the consumer 15 may consider different options. One option is for the consumer 15 to purchase the medication and other items of interest from a different store than the pharmacy 14 or the store 16. Another option is to acquire the medication and other items from different locations. As described herein, the prescription processing system 30 can reconcile the delivery of the medication and other items, regardless of whether they are purchased from different stores. Another option is to only purchase the medication from the pharmacy 14 and to forgo the purchase of other items.

At block 108, the order is filled. This includes the coordinated delivery of the medication and items of interest under a single delivery order.

At block 112, a notification is generated by the prescription processing system 30 indicating of the delivery of the prescribed medication and other items. Other notifications may include recommendations on additional items that may be of interest to the consumer 15, for example, a cross-selling feature, or warnings related to possible conflicts between the medication and the other items.

Figure 4:
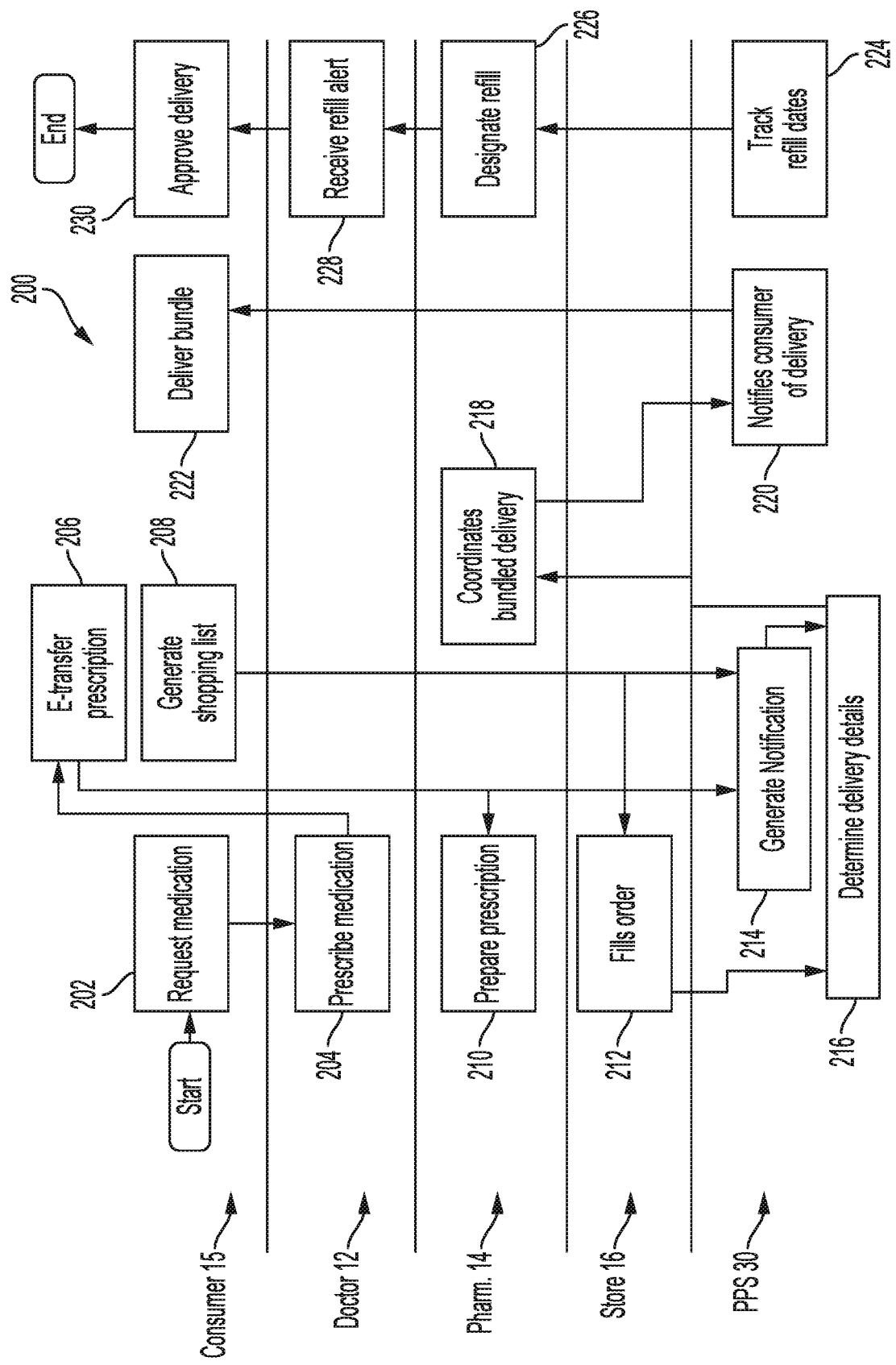
FIG. 4 illustrates an exemplary process flow for a prescription delivery service, in accordance with some embodiments.

FIG. 4 is a process flow 200 for a prescription delivery service, in accordance with some embodiments. Some or all of the method 100 can be performed at the prescription processing system 30 of FIGS. 1 and 2, and/or other elements of the environment illustrated in FIG. 1. The method 100 can be governed by instructions that are stored in a memory device of the prescription processing system 30 of FIGS. 1 and 2, and/or other elements of the environment illustrated in FIG. 1, and executed by a hardware processor of the prescription processing system 30 of FIGS. 1 and 2, and/or other elements of the environment illustrated in FIG. 1.

At block 202, a source of medication is requested for a customer 15. The request may be made by the customer 15, or another authority may request medication on behalf of the customer 15, for example, a doctor. Accordingly, at block 204, a doctor 12 prepares a prescription for the requested medication.

The consumer 15 may receive an electronic version of the prescription, for example, generated by the doctor's computer 42. At block 206, the prescription is provided to the pharmacy 14 for preparing (block 210) the prescription. In some embodiments, the prescription is automatically transferred to the pharmacy 14.

At block 208, the consumer 15 generates a shopping list, for example, by executing a software application and entering the list electronically on an electronic device 17.

At block 212, a store 16 fills an order corresponding to the items on the shopping list.

At block 214, a notification may be generated in response to the prescription processing system 30 receiving data related to at least one of the prescription or the shopping list. The notification can include recommendations on additional items that may be of interest to the consumer 15 based on the prescribed medication. For example, a recommendation to purchase bottled water may be generated when the prescription includes medication in a pill format. Other notification may relate to a conflict between the purchased items on the shopping list and the prescribed medication. For example, a warning may be generated when the shopping list includes alcohol, and the prescribed medication includes instructions not to consume alcohol, noting that the prescription processing system 30 may store the medication instructions or retrieve medication instructions from the pharmacy computer 44 or other remote storage device.

At block 216, the prescription processing system 30 may determine delivery details with respect to the purchased medication and additional items, regardless of whether the medication and additional items are purchased together, for example, at the pharmacy, or purchased separately at different stores. The prescription processing system 30 may provide a mailing address and other information to the pharmacy 14, store 16, and/or other entity shipping the medication and the other items. At block 218, the pharmacy computer 44 receives the bundled shipment information from the prescription processing system 30 and coordinates with the store 16, for example, via the prescription processing system 30, to ship the prescription and other items together under a single order in accordance with the bundled shipment information, so that the consumer 15 pays for a single delivery. In other embodiments, the pharmacy 14 and store 16 communicate with each other by phone, email, or other communication.

At block 220, the prescription processing system 30 generates a notification that can sent to an electronic device 17 of the consumer 15 indicating of the delivery of the prescribed medication and other items.

At block 222, the medication and other items are delivered together at the predetermined delivery location. The medication and other items can be placed in a special package that addresses requirements of the medication and/ or other items, for, a temperature controlled box 21 (see FIG. 1) or related container for housing the medication during delivery. Although a box 21 is referred to, other storage devices may equally apply, for example, containers that are configured differently than a square or rectangular box. Although the medication and items are delivered together, they may be placed in the same or separate packaging, for example, different containers.

The special package, or temperature controlled box 21, for example, may include an inner volume for storing the medication and/or other items during delivery by the vehicle 19, and a door for opening and closing the box 21, i.e., exposing the inner volume or enclosing the items therein. The box 21 may include one or more adapters, sensors, monitors, regulators, controllers, and so on. The box 21 may be part of or otherwise configured to deliver items of interest between locations in the autonomous vehicle 19.

For example, an adapter may be coupled to an air conditioning unit and/or heating unit for cooling and/or heating the inner volume of the box or otherwise providing a desired temperature. Other adapters may be coupled to a temperature regulator, humidity regulator, a power source, security panel, and so on for providing a desired environmental feature.

In some embodiments, the box 21 may include an internet of things (IoT) device or computer interface that allows a user to log in and set the temperature, or to configure the system so that the temperature is adjusted automatically, for example, a temperature controller that changes the temperature to accommodate the package placed in a compartment or sub-compartment of the inner volume of the box 21 in response to temperature readings provided by a temperature, pressure, humidity, and/or other sensor. The temperature controller may generate temperature information on a regular basis to an electronic device in possession by a user, for example, output temperature information regarding the interior of a storage compartment every 5 minutes to the prescription processing system 30 and/or computer servers 42, 44, and 46.

As described herein, the inner volume, or storage compartment, of the box 21 may be temperature-controlled, for example, heated or cooled. In some embodiments where the storage compartment includes multiple sections or sub-compartments, the sub-compartments are maintained at one temperature by a sensor, while another sub-compartment is maintained at a different temperature.

In another example, the box 21 may include a monitoring device that controls and monitors an operation of the box 21, for example, environmental conditions and status of contents, a power source, location tracking, access and security, and so on. Thus the box 21 may monitor medication and/or store items that may include perishable goods, such as milk. In some embodiments, the box 21 includes a communication device for communicating with the vehicle 19. For example, a BLUETOOTH™ interface may exchange transactional data with the vehicle 19, such as sending a signal that the box 21 and its contents have been received.

Further, in use, the box 21 may communicate the status of contents as well as the environment of the inner volume of the box 21 to the prescription processing system 30, for example, communicate messages regarding location, temperature, humidity, package status, delivery status, security panel access, removal or insertion of products, and the like. In other embodiments, this communication may send information from the box 21 to the vehicle 19.

Also in use, the box 21 may connect to a delivery vehicle 19, such as an autonomous vehicle by connecting to the autonomous vehicle systems or other delivery vehicle systems. For example, the box 21 may include an adapter that allow for environment control agents to be deployed into the inner volume of the box 21, connections to allow for transference of power from the vehicle 19 to the box 21 that may power the boxes 21. This may allow for seamless connection and disconnection from vehicle systems, wherein the connection between the vehicle system and the box 21 may be tracked; and the connection between the delivery vehicle system may be monitored for connective security.

In some embodiments, the box 21 may include a delivery encryption system comprising a blockchain for package tracking and authentication. The blockchain may include an ongoing chain hashed with key addresses along the chain of custody, including hashing with a seller private key address, a courier private key address and a buyer private key address, but not limited thereto. Here, a blockchain registers contents such as a medication or other pharmacy item and/or other grocery items to be delivered and placed within the inner volume of the box 21; and registers and authenticates the contents within the inner volume as the box 21 moves through a supply chain or otherwise between locations of interest.

In embodiments, the blockchain associated with the contents placed in the box 21 dynamically adjusts to account for the cold chain status of the product 50 as the smart package 10 moves through a supply chain. The chain block of a delivery encryption system may track and authenticate each of the contents, for example, both pharmacy and non-pharmacy items in the box 21.

In some embodiments, if the consumer 15 has availability for refills, the prescription processing system 30 can track the refill information and notify the consumer, based on assumed use according to the prescription, for example, 2 pills per day, when a refill is being processed. Automatic replenishment of a prescription is possible based on quantity, frequency, so on. When refills are performed in this manner, the refill medication may likewise be bundled with other items for delivery under a single order in a similar manner as described in other embodiments. In some embodiments, automatic replenishment is derived from replenishment data included in an original prescription blockchain.

Accordingly, at block 224, the prescription processing system 30 tracks refill dates and/or other refill information based on usage or consumption of prescribed medication. The prescription processing system 30 may generate an alert that is sent to the pharmacy computer 44 if determined usage amounts are different than a predetermined threshold or prescription amount.

At block 226, the pharmacy 14 may designate a refill in accordance with the prescription processing system. In some embodiments, the prescription processing system 30 tracks the pharmaceutical information, which includes a refill status that can be automatically tracked and fulfilled by the system 30.

At block 228, the doctor may receive at the doctor's computer 42 an alert that the pharmacy is initiating a refill in according with refill instructions generated by the prescription processing system 30. At block 230, the consumer 15 may approve the received delivery. The bundle may be created according to customer specific orders. The customer can turn away or reject a product or accept a product. The refill is tracked and staged but refills will be sent by customer request but not before refill date stated in prescription information.

In some embodiments, once a prescription has been submitted by the doctor or affiliation to the pharmacy 14, a blockchain of the patient's prescription may be created as described above. Here, any and all replenishments or refills for the prescription may also be included with this blockchain. From this refill information, a peer-to-peer ledger system and the application used by the retailer for this service will parse messages to the consumer patient 15 when a prescription requires a refill. This may be done at the suggested time of refill by the doctor and their affiliates, or may be accomplished by specific defined time windows by the retailer and a corresponding database or other repository accessible for performing the required functions.

When a prescription requires refill or replenishment and the customer has agreed to have this refilled or replenished, this may initiate a subsequent block, which will share information relating to the prescription with the pharmacy 14. The pharmacy will have the same functionality for procurement of the prescription, as well as a referral system.

In summary, automatic replenishment may be accomplished through data structured into a prescription blockchain. When the prescription has depleted or expired, a customer may be notified through the peer-peer ledger system of a prescription need. When selected by the patient, the prescription may be automatically replenished through the blockchain information, which will allow the prescription to be transmitted to a pharmacy. The pharmacy can then complete the processing of the prescription and send notification to the patient; or automatic delivery may also be featured within the blockchain data.

In some embodiments, information, for example, described in examples herein, may be shared, executed, and distributed through the application. In some embodiments, information, for example, described in examples herein, may be shared, executed, and distributed through the blockchain system by way of a peer-peer ledger system, identifiers, profiles, and keys.

In some embodiments, systems and methods provided that allows for the processing of a prescription through the blockchain's peer-peer ledger system where a patient has control of their records, allowing a prescriber of medication to transmit a prescription to the peer-peer ledger system. The patient can review the prescription from the peer-peer ledger system. The patient can select pharmacy providers from the peer-peer ledger system, which has a network of pharmacy providers with criteria, such as location, time, availability. Then, the patient can select from methods for pickup, delivery, or a trusted pickup. The methods may contain information on the entity stored on the peer-peer ledger system along with criteria, such as location, time, availability, and so on.

As described above, additional purchases may be added to a prescription as part of a delivery. Here, products and prescriptions may have blockchain identifiers that may be processed to determine similar products for recommendations. When selected by the customer, additional items may be added to the prescription delivery or pickup as a bulk order.

Figure 5:
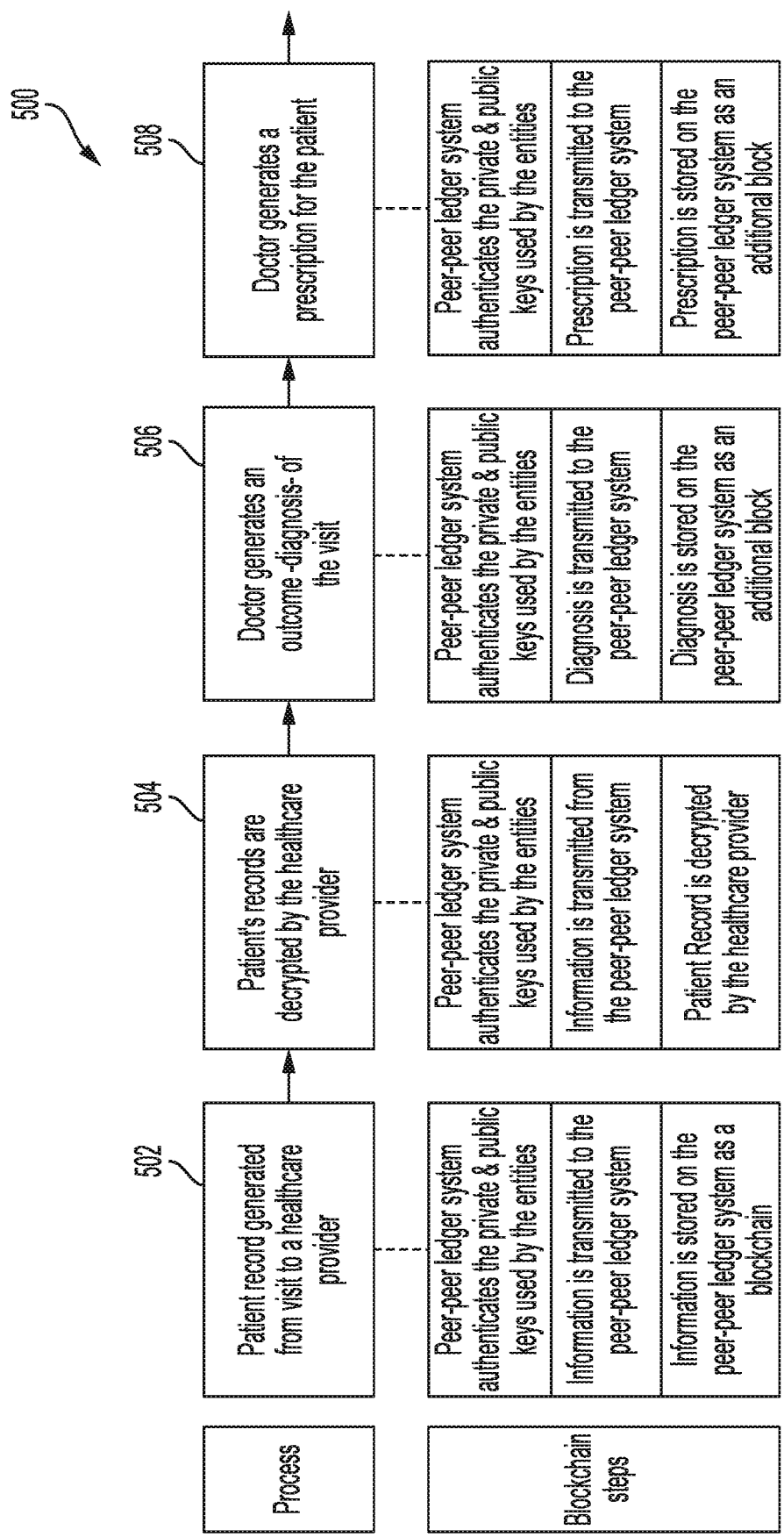
FIG. 5 illustrates an exemplary process flow for processing patient records and prescription data, in accordance with some embodiments.

FIG. 5 is a process flow for processing patient records and prescription data, in accordance with some embodiments. As described in some examples, a process 500 may include method steps of generating (502) a patient record related to a visit to a healthcare provider, decrypting (504) the patient record, generating (506) by a doctor computer an outcome of the visit, and generating (508) a prescription for the patient. Some or all steps 502, 504, 506, 508 may include a set of blockchain steps performed by a blockchain system include special purpose processors and memories, illustrated in FIG. 5.

Figure 6:
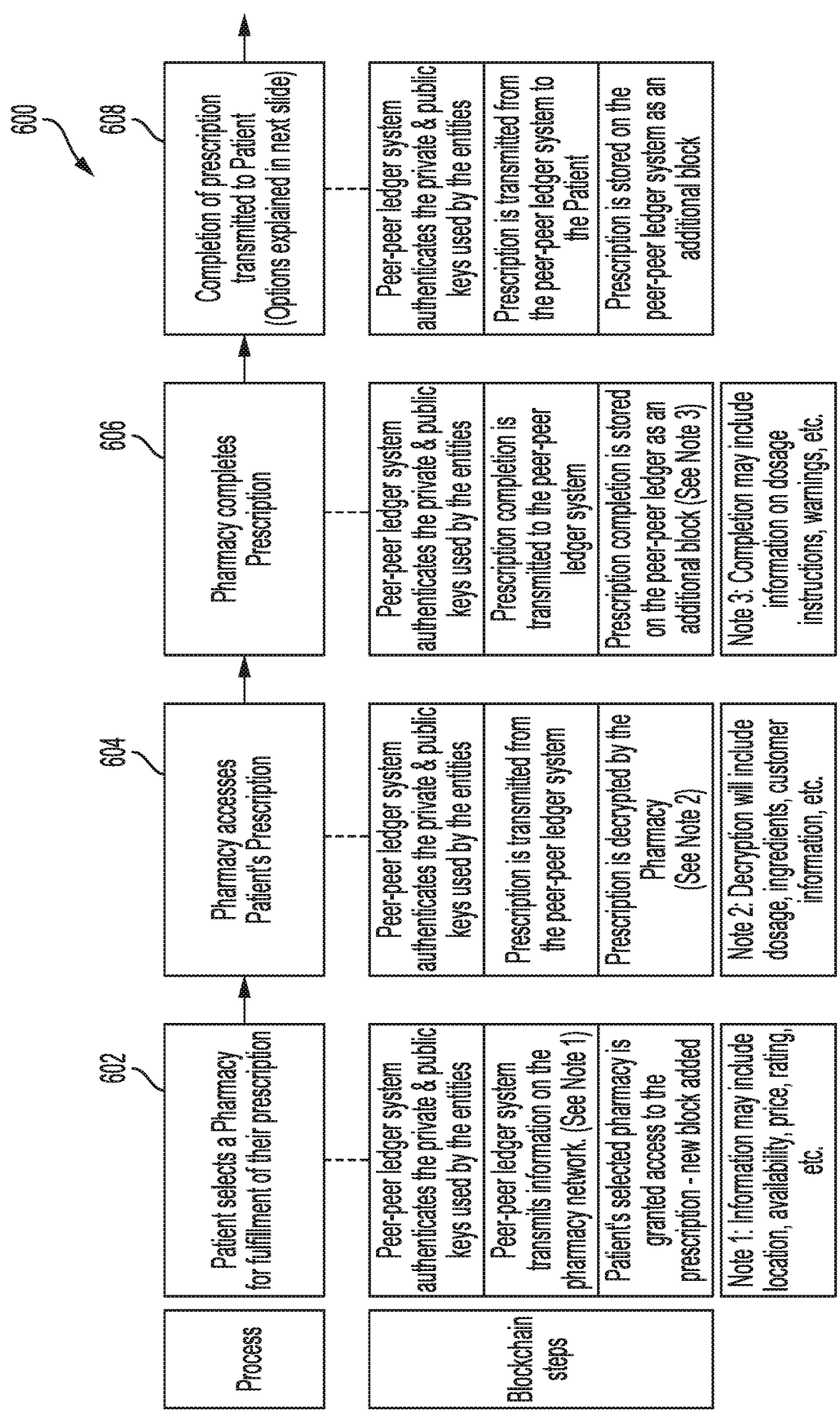
FIG. 6 illustrates an exemplary process flow for pharmacy fulfillment of a prescription, in accordance with some embodiments.

FIG. 6 is a process flow for pharmacy fulfillment of a prescription, in accordance with some embodiments. As described in some examples, a process 600 may include method steps of selecting (602) by a patient at a computer a pharmacy for fulfilling a prescription, accessing (604) by a selected pharmacy the patient prescription, completing (606) at the pharmacy computer the prescription, and completing (608) the prescription transmitted to the patient. Some or all steps 602, 604, 606, 608 may include a set of blockchain steps performed by a blockchain system include special purpose processors and memories, illustrated in FIG. 5.

Figure 7:
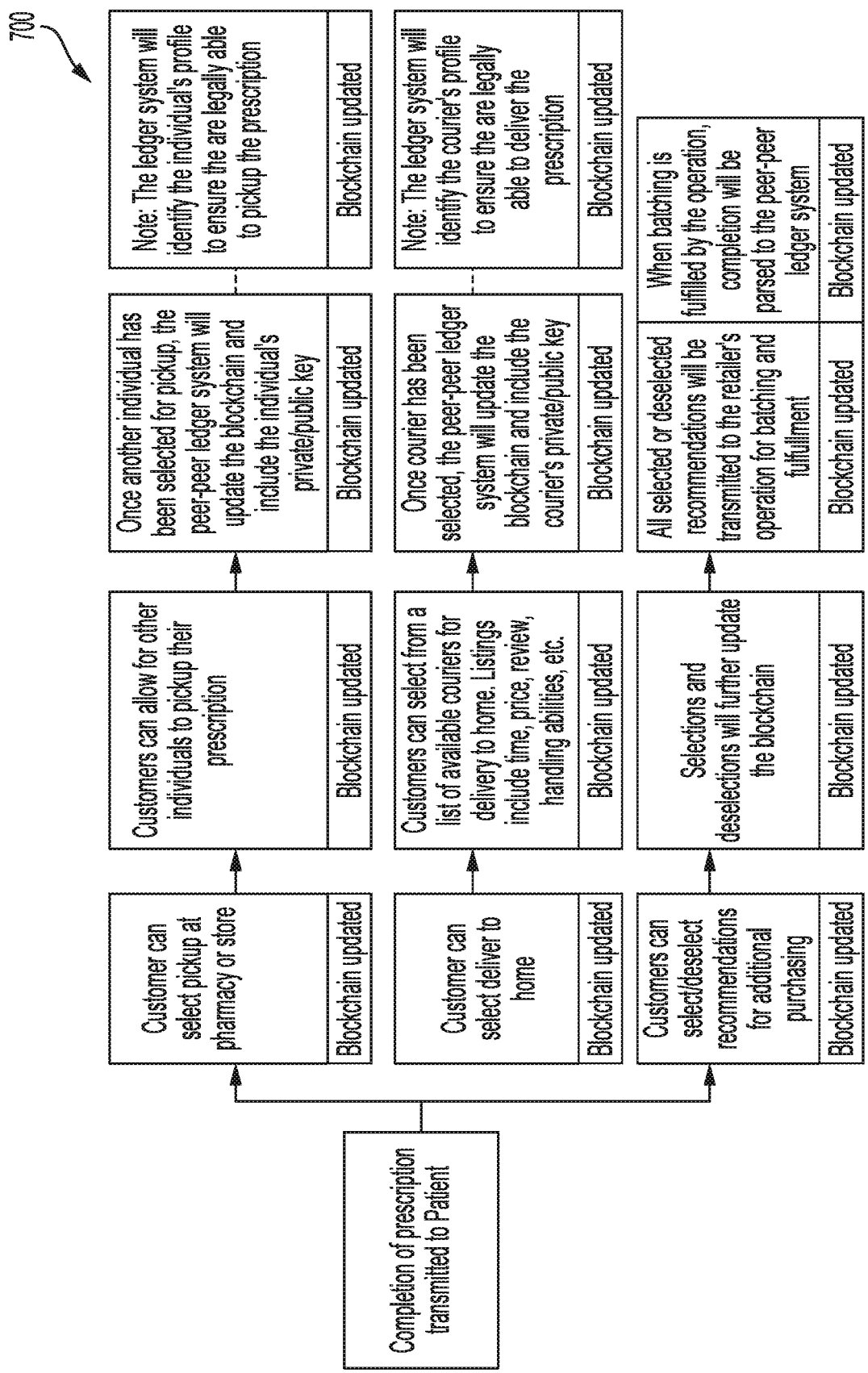
FIG. 7 illustrates an exemplary patient decision process flow after a prescription fulfillment, in accordance with some embodiments.

FIG. 7 is a patient decision process flow after a prescription fulfillment, in accordance with some embodiments. A process 700 may be performed after the prescription fulfillment process 600 illustrated and described with respect to FIG. 6, in particular, after completion of a prescription that is electronically transmitted from a prescription fulfillment computer for example at a pharmacy to a patient's computer, for example, laptop computer, smartphone, and so on. In each step of the process 700, a related blockchain is updated, for example, processed at a hardware computer.

Figure 8:
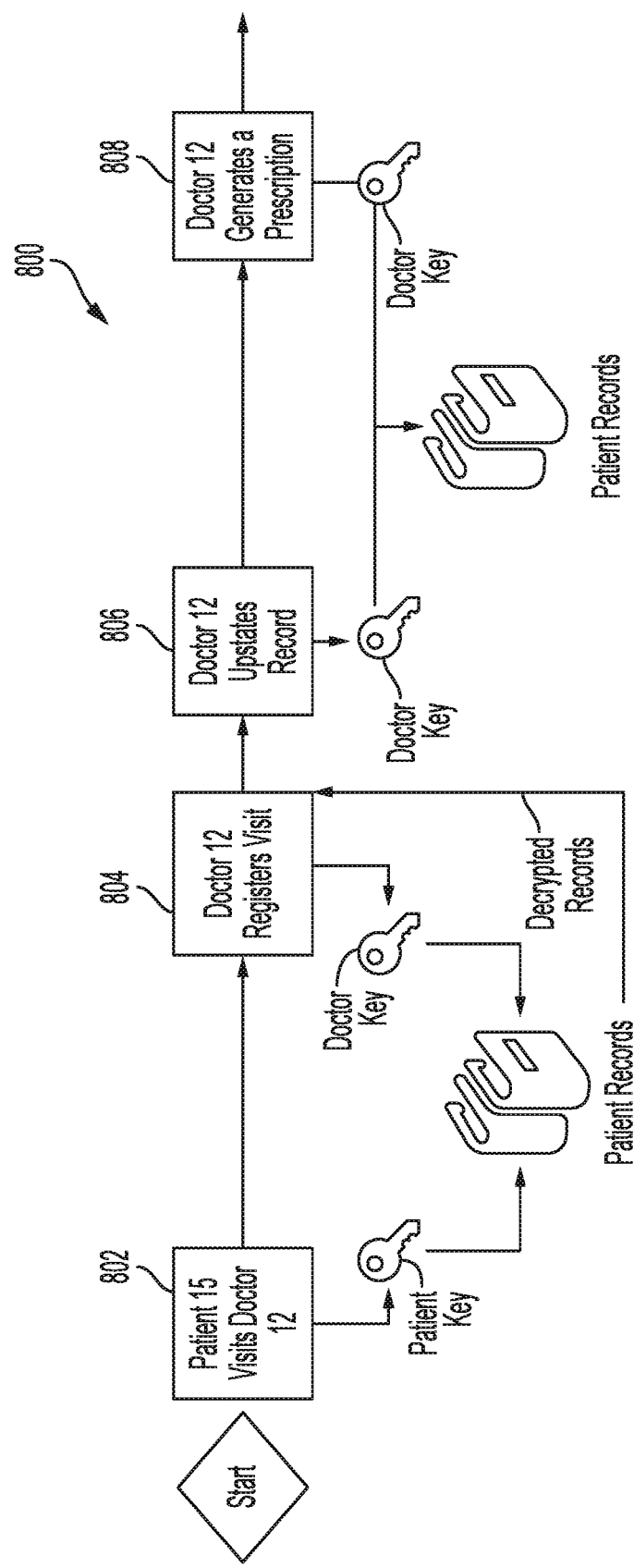
FIG. 8 illustrates an exemplary process flow for a prescription fulfillment, in accordance with some embodiments.

FIG. 8 is a process flow for a prescription fulfillment, in accordance with some embodiments. In describing FIG. 8, reference may be made to elements of FIGS. 1-7. As described in some examples, a process 800 may include method steps of a patient 15 visiting (802) a doctor 12, the doctor 12 registering (804) the visit, the doctor 12 updating (806) a patient record, and the doctor 12 generating (808) a prescription. Steps 802-808 may be similar to steps 502-508 of FIG. 5, and therefore, details are omitted due to brevity. A security key, e.g., a patient key or doctor key, is required at each step 802-808 to complete the respective step where accessing or decrypting/encrypting patient records is concerned. The process flow may include the use of a system comprising a blockchain for authentication. The blockchain may include an ongoing chain hashed with key addresses along the chain of custody, including hashing with a private key address, but not limited thereto. Here, a blockchain registers visit-related information, records, prescription details, and/or other information exchanged in the process 800.

Figure 9:
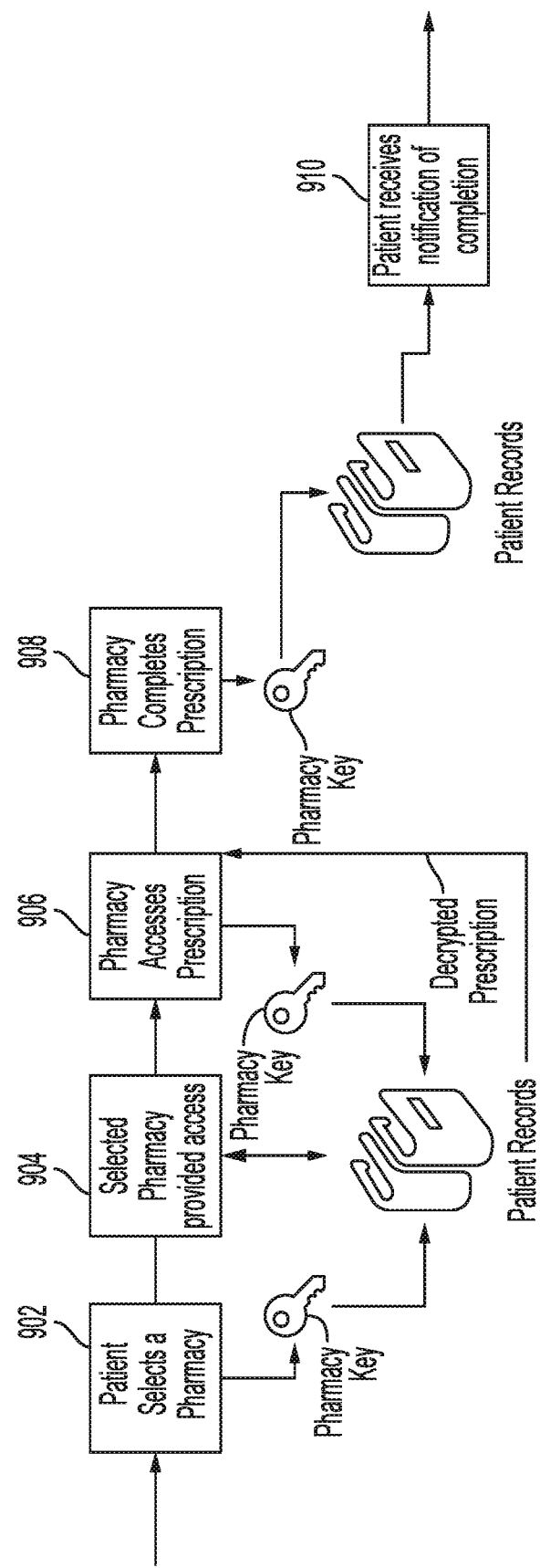
FIG. 9 illustrates an exemplary process flow for a prescription fulfillment, in accordance with some embodiments.

FIG. 9 is a process flow for a prescription fulfillment, in accordance with some embodiments. In describing the process 900 of FIG. 9, reference may be made to elements of FIGS. 1-8.

As described in some examples, a process 900 may include method steps of a patient 15 selecting (902) a pharmacy, which may occur after performing the process 800 of FIG. 8. The process 800 may further comprising providing access (904) by the selected pharmacy, accessing (906) a prescription, completing (908) the prescription, and receiving (910) a notification of the prescription. Steps 902-908 may be similar to steps 602-608 of FIG. 6, and therefore, details are omitted due to brevity. A security key, e.g., a patient key or doctor key, is required at each step 902-908 to complete the respective step where accessing or decrypting/encrypting patient records is concerned.

An example of an operation performed by the method steps of FIGS. 8 and 9 may include the following. Secure processing of sensitive patient data may be performed by an electronic device at a first location, for example, as the patient visiting the doctor's office. An electronic device at the doctor's office decrypts and accesses the patient's record. The doctor submits any new records to the patient's record through the peer-peer ledger system. The doctor submits a prescription to the peer-peer ledger system. The patient selects a pharmacy from the peer-peer ledger system and provides access to this pharmacy for prescription processing. The pharmacy completes and notifies the patient of the completed prescription through the peer-peer ledger system. The retailer suggests additional products for purchasing by identifying the prescription identifier and comparing its stored information with products. The patient selects methods for pickup or delivery through the peer-peer system, which may allow for specific access to the record. Further, the pharmacy and the retailer establishment are also communicated and transmitting with the same peer-peer ledger system. This may also include doctors and patients and/or other interested parties.

The systems and methods in accordance with some embodiments allows for the transmission, communication, procurement, and authentication of prescription information to be accomplished by a cryptography system facilitating a peer-peer ledger system, which controls access to the records and allows for iterations to be made. It is not limited to doctors and patients but will allow access for doctors, patients, pharmacies, couriers, and retailer.

The systems and methods in accordance with some embodiments generates alerts and messages from updates made to the peer-peer ledger system where the peer-peer ledger system communicates updates directly with authorized entities, which may include patients, pharmacies, doctors, retailer, couriers, and so on.

The systems and methods in accordance with some embodiments allows the peer-peer ledger system to store and distribute information on pharmacies available for processing the prescription, which may include information on location, pricing, availability, etc.

The systems and methods in accordance with some embodiments allow for blockchain product identifiers to contain data on the temperature requirements for a given product. It may further distribute this information to a temperature controlled device through active scanning, barcode scanning, private-key scanning, peer-peer ledger transmission, etc. Once the device has identified the product and its temperature requirements, it may control the temperature with its technology; all of which may be further distributed to the peer-peer ledger system to include real-time status, etc.

The systems and methods in accordance with some embodiments allow for pharmacy inventory levels (availability) to be transparent to the patient when selecting a pharmacy; further, the recommendation engine determines products for recommendation based on the prescriptions product identifier, which will include availability of items. All additions made to the order will further update the original prescription blockchain.

As discussed above, patients, pharmacies, and medical personnel may all have both public and private keys which are used to help validate and verify blocks within a blockchain. In cryptocurrencies, for example, a user's private key is often used to generate a signature for each blockchain transaction. The private key can be used to derive the user's public key, which in turn is transformed with a hash function to produce an address available to others.

However, systems configured according to this disclosure can improve the security of a prescription by combining multiple public keys together, then hashing that combination to produce a unique result. For example, the public key of a medical professional creating a prescription may be combined with the public key of a patient, then the combined keys of the patient and medical professional may be hashed. The output of the hash function may then be transmitted to a pharmacy for fulfillment of the prescription. The pharmacy is granted knowledge of the public keys of both the doctor and the patient, and is thereby able to verify the results of combined hashed output.

When fulfilling (preparing and distributing) the prescription, the pharmacy can combine its public key with the public keys of the medical professional and the patient (a three-way public key combination). This three-way public key combination is then hashed, and added to the blockchain. Preferably, in order for the patient to retrieve the prescription, presentation of the patient's private key will need to be given to a computer system connected to the distributed ledger at the pharmacy.

In some configurations, the hashed output of the combination of the medical professional's public key and the patient's public key can take the form of a token which is not immediately verified by the distributed ledger. Instead, the token is transferred to an account belonging to the patient, and the user can then present the token at any participating pharmacy. At that point, the token will transfer to the pharmacy, the pharmacy will verify the prescription using the token and also based on stored public keys of the medical professional and the patient. If everything is confirmed as valid (based on verification by a distributed computing network using a distributed ledger), the pharmacy will redeem the token and add a record of the transaction to the blockchain. The record can take the form of a new block which contains the public keys of the patient, the medical professional, and the pharmacy, as well as information about the prescription, the date, the address of the pharmacy, etc. The token would no longer be usable after that single occurrence.

In some configurations, the system can have the patient's profile stored, along with information such as allergies, pharmacy preferences, other prescriptions, drug history, etc. In addition, the system can have information stored about the pharmacy, such as store hours, drive-through hours, after hours locations, human delivery options, drone delivery options, etc. Using this information, the system can assist the patient regarding where the patient should go to fulfill a received token.

The patient may also choose to include other products in the purchase of the prescription, with information regarding those additional products being included when the combination of the public keys are hashed. The resulting output (multiple public keys+information regarding at least one restricted product+information regarding additional products which may or may not be restricted) can then be added to the blockchain and distributed across the distributed ledger.

In some configurations, additional data which may be included in the blockchain can be non-key (not a public or private key) information which further verifies the transaction. For example, video of the delivery of the prescription can be recorded and the video, or aspects of the video, can be added to the blockchain. Alternatively, the blockchain can contain a link to a database of the video, such that the video itself is not stored in the blockchain, only a link to the video. In yet another possible configuration, the blockchain may contain a sidechain linked to the main chain, with the sidechain containing the video. This sidechain may be restricted in terms of distribution within the distributed ledger, but its existence may be fully distributed with the distributed ledger. Such an arrangement allows minimal or reduced memory requirements while still ensuring complete access to the information should it be required. Other non-essential data which may be stored similarly may include co-delivery number, route, elapsed time, delivery endpoint type, delivery completed, delivery returned, time of prescription fulfillment, etc.

The combination of multiple public keys (as well as other information) as inputs into a hash function results in a multi-layered security system. As discussed, the primary area of intended usage is prescription medicines. However, other areas where this multi-layered security system may be useful are items which require special authorizations to distribute and/or receive products. For example, a fuel truck for depositing fuel at gas stations needs a special permit to transport gasoline, as does the gas station to sell gasoline. The combined public keys could be used in verifying a transaction where a gas truck deposits gasoline at a gas station. Other exemplary, non-limiting areas where this multi-layered security could be used include organic crop vendors with licensed restaurants, specific types of firearms, legal proceedings, airport security, etc.

Having described how these improvements to security occur, the disclosure next turns to the specific examples provided in FIGS. 10-14.

Figure 10:
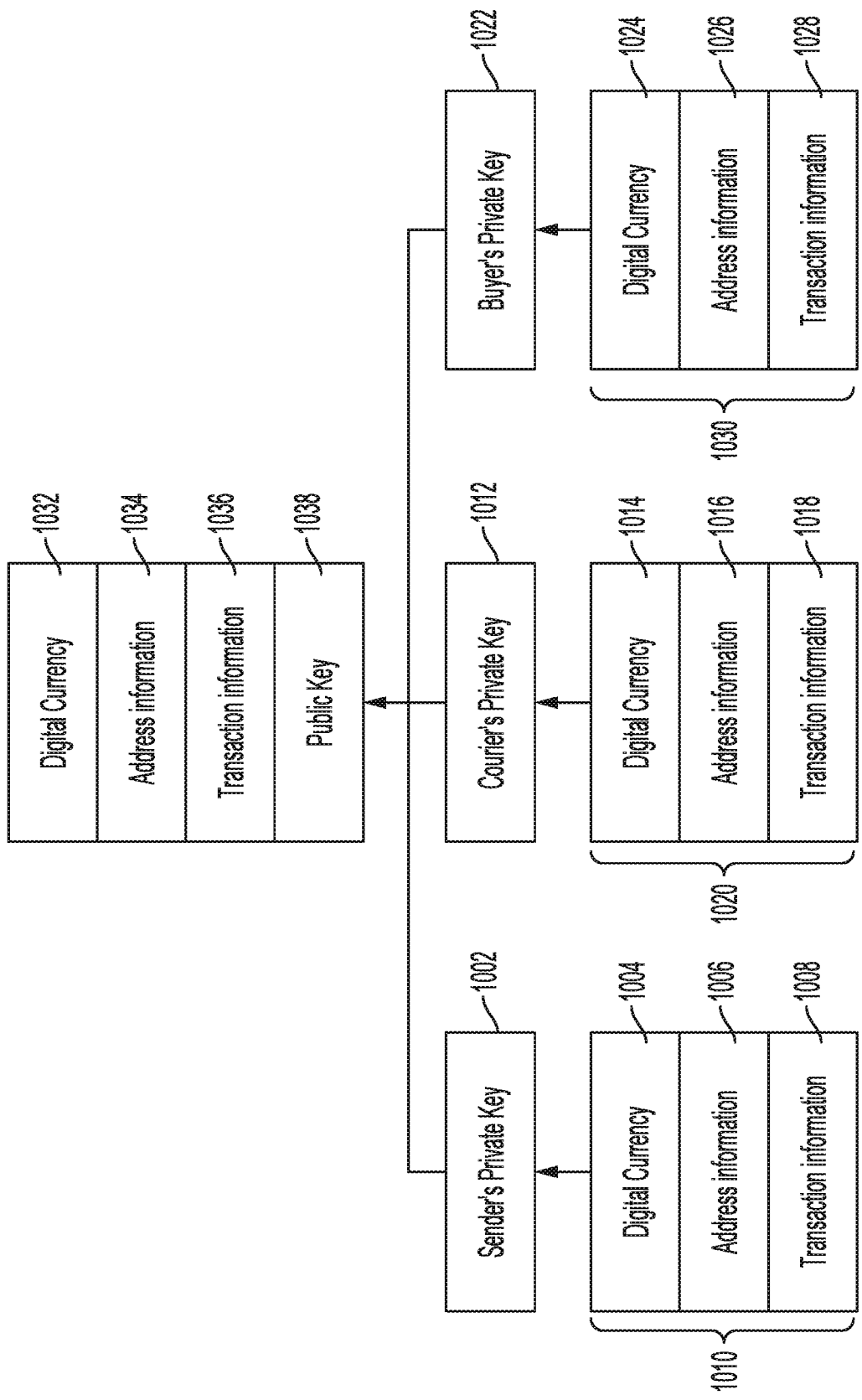
FIG. 10 illustrates a first exemplary cryptographic delivery system.

FIG. 10 illustrates a first exemplary cryptographic delivery system. In this example, three separate individuals are being used in a transaction: a sender, a buyer, and a courier transporting goods from the sender to the buyer. For each individual in the process, that individual's wallet information, contact information, and authorization for their aspect of the transaction can be recorded and transformed into a private key. For example, as a doctor (in this example, a sender) transmits a prescription, the doctor's digital currency 1004, address (or other contact) information 1006, and the prescription information (transaction information) 1008 can be gathered together 1010, then combined with the doctor's private key 1002. This algorithmic transformation of the private key 1002 with the combined data 1010 results in a public key 1038.

Similar transformations of a courier's data 1020 (including the digital currency 1014, the address/contact information 1016, and transaction information 1018) with the courier's private key 1012, and the buyer (patient) data 1030 (including the digital currency 1024, the address/contact information 1026, and transaction information 1028) can likewise occur.

In some configurations, each of these transformations can individually result in a public key 1038, which can then be hashed in a manner which allows those computing systems with access to the public key to verify the transactions. However, in addition to those individual public keys, systems configured according to this disclosure can combine the public keys created from the individual private keys 1002, 1012, 1022, then hash this combination of the public keys to form an address, or block, available for addition to the blockchain. Those systems which do have access to the public keys would be able to verify the transaction, without having access to the private keys, such that information about the digital currency 1032 spent, the address or other contact information 1034 is provided, and the transaction 1036 can be accessed/verified by third party computing systems.

Figure 11:
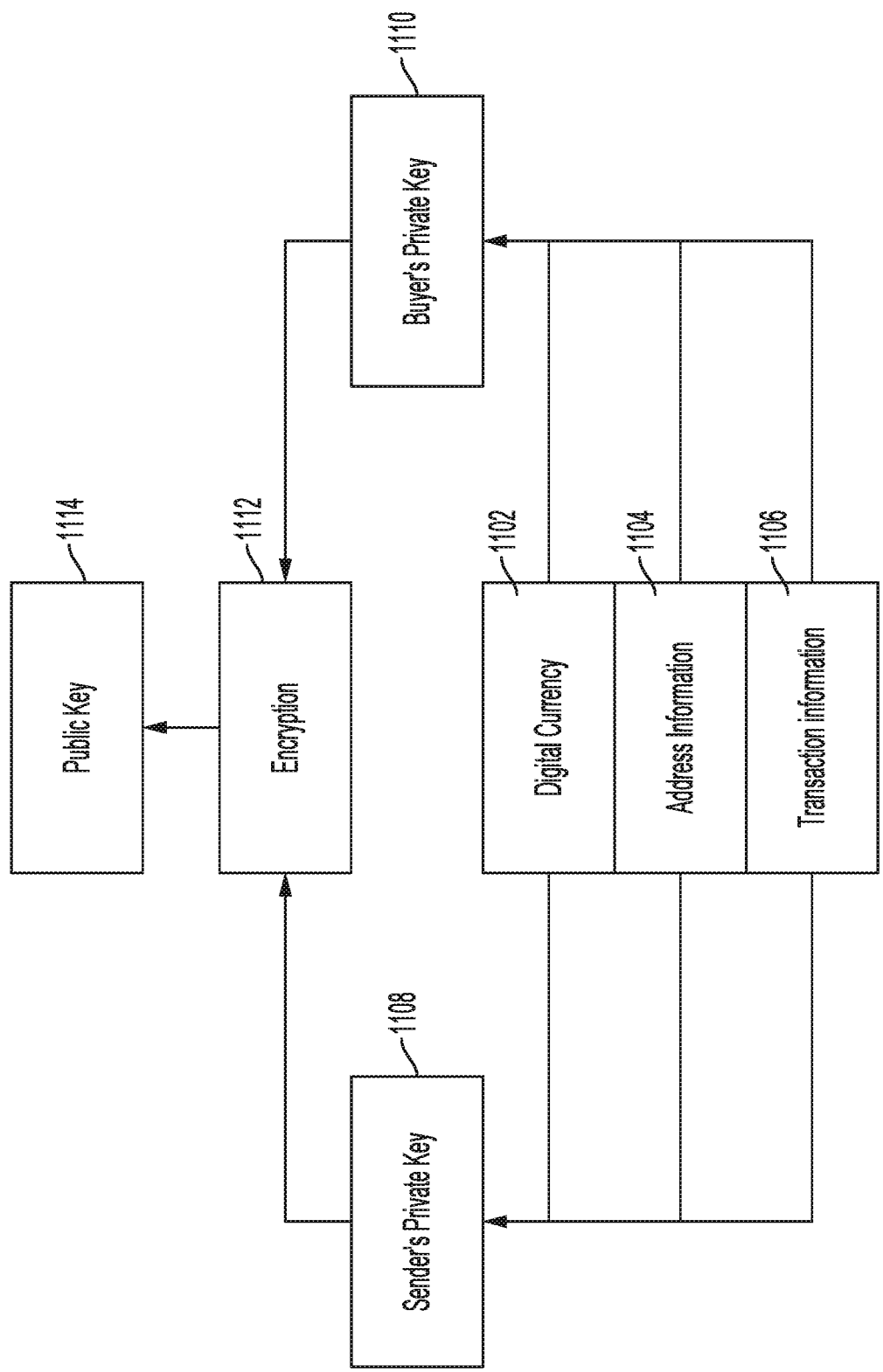
FIG. 11 illustrates a second exemplary cryptographic delivery system.

FIG. 11 illustrates a second exemplary cryptographic delivery system. In this example, the data associated with a transaction, such as the digital currency 1102 being exchanged, the contact/address information for the parties involved 1104, and the transaction information (e.g., what pharmaceutical is being prescribed) 1106 are transformed using the sender's private key 1108 as well as the buyer's private key 1110. These dual transformations result in two distinct pieces of data which are combined and encrypted 1112, resulting in a public key 1114 which is made using data from both private keys. The encryption 1112 may, in some configurations, be a hash function which uses both the sender's private key 1108 and the buyer's private key 1110 as inputs. In yet other configurations, additional data about the transaction may be separately included in the inputs to the encryption/hash function 1112 to generate the resulting public key 1114.

Figure 12:
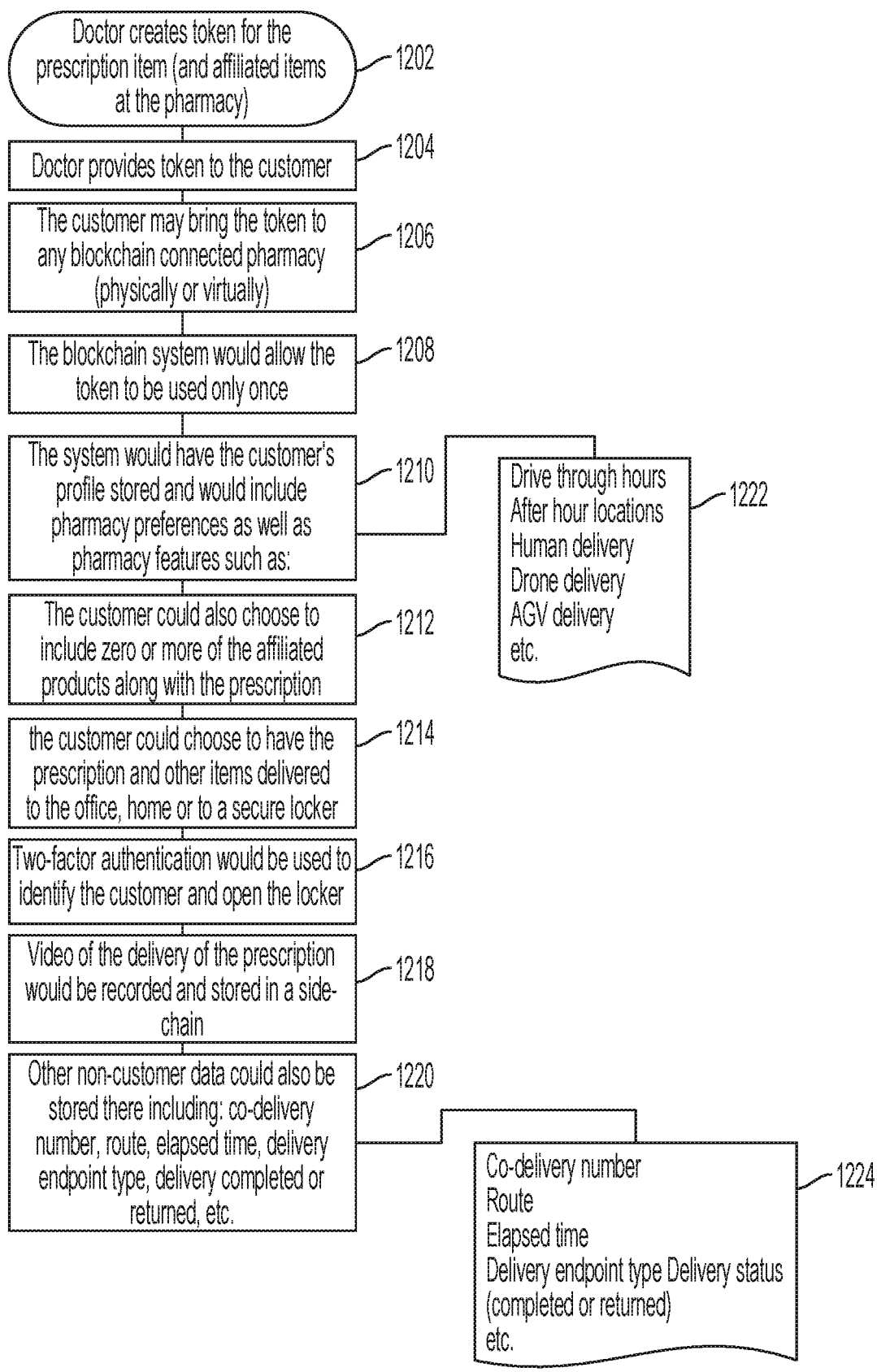
FIG. 12 illustrates an exemplary process flow for prescription fulfillment using a token.

FIG. 12 illustrates an exemplary process flow for prescription fulfillment using a token. This token is created when a doctor creates a prescription for an item at a pharmacy (and affiliated items at the pharmacy) (1202). The doctor provides the token to the customer (1204). In one case, this transfer may be restricted to using near-field communications (communications which attenuate to unusable after 1-2 meters) between two mobile devices. For example, the doctor could authorize a prescription via a tablet computer (or other mobile device), the tablet could generate the token using the doctor's private key and information about the patient and the prescription, and then transfer the token to the patient's smartphone.

The customer may then bring the token to any blockchain connected pharmacy (physically or virtually) (1206). The blockchain system which is used to generate/redeem the token only allows the token to be used once (1208). This blockchain system can have the customer's profile stored and include pharmacy preferences/features (1210), such as drive through hours, after hours locations, human delivery options, drone delivery options, AGV (Automated Guided Vehicles) delivery options, etc. (1222). The customer may also choose to include additional products along with the prescription (1212) in the order. That is, the customer may also choose to purchase other products and include them in the same transaction record. Possible reasons for this may include simplifying the transaction process for the customer (only one purchase instead of two or more), or documenting a record of purchases for later reimbursement/insurance purposes. The customer may further choose to have the prescription (and other items) delivered to the office, home, or a secure locker (1214). A two factor authentication system can be used to identify the customer and open the locker (1216). Video of the delivery of the prescription may be recorded and stored in a side chain (1218). Other non-customer data can also be stored in the side chain, such as co-delivery number, route used for the delivery, elapsed time (for transit and/or since order), delivery endpoint type (house, apartment, office, open field, mobile home, etc.), delivery completed or returned, etc. (1220, 1224).

Figure 13:
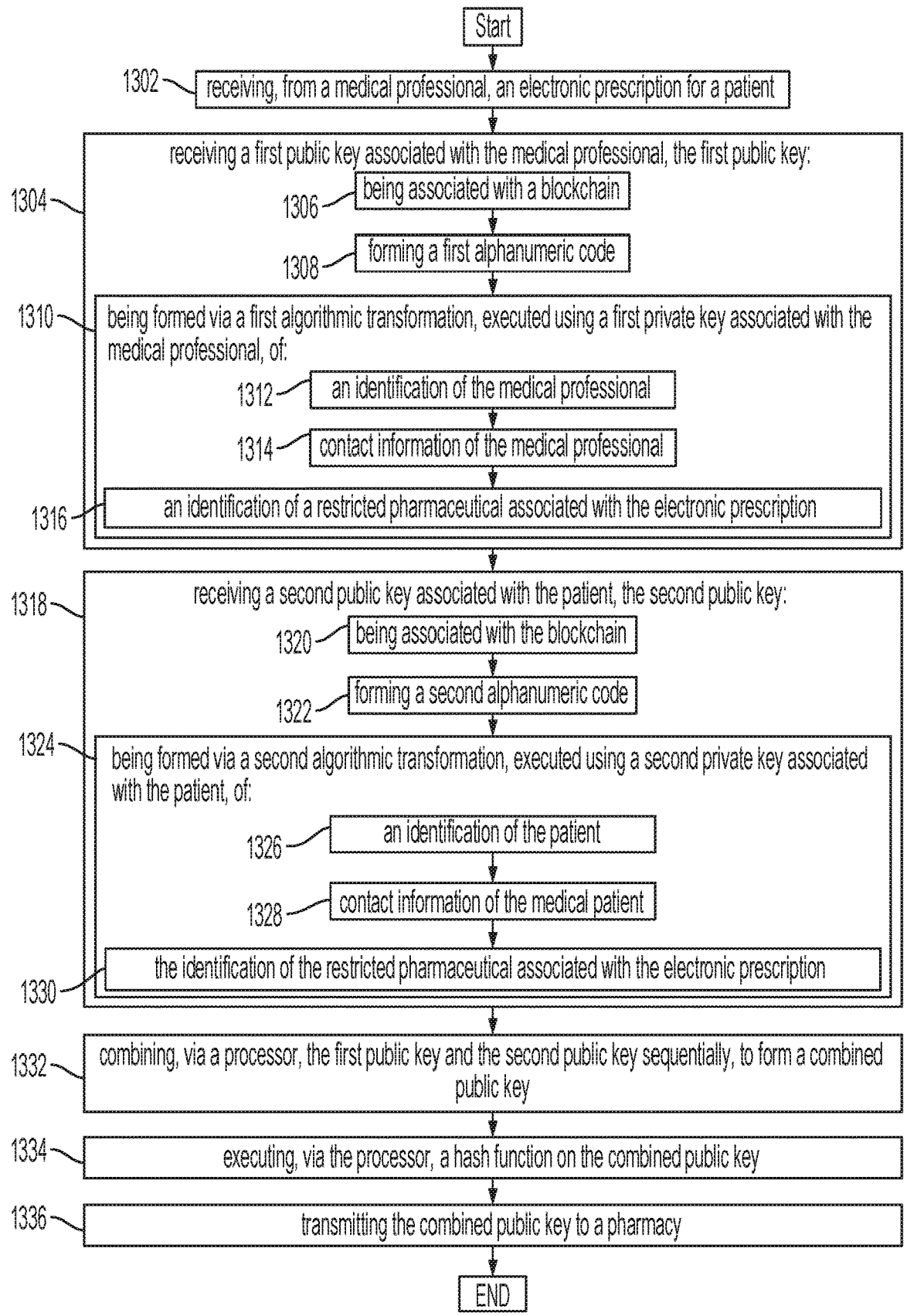
FIG. 13 illustrates an exemplary method embodiment.

FIG. 13 illustrates an exemplary method embodiment. In this example, a distributed ledger/blockchain system is used to combine multiple public keys together, which are then transmitted to a pharmacy for prescription fulfillment. First, the system receives, from a medical professional, an electronic prescription for a patient (1302). The system also receives a first public key associated with the medical professional (1304), the first public key: being associated with a blockchain (1306), forming a first alphanumeric code (1308), and being formed via a first algorithmic transformation, executed using a first private key associated with the medical professional (1310). The algorithmic transformation uses as inputs an identification of the medical professional (1312), contact information of the medical professional (1314), and an identification of a restricted pharmaceutical associated with the electronic prescription (1316).

In parallel or sequentially with the reception of the first public key, the system also receives a second public key associated with the patient (1318), the second public key: being associated with the blockchain (1320), forming a second alphanumeric code (1322), and being formed via a second algorithmic transformation, executed using a second private key associated with the patient (1324). This algorithmic transformation similarly uses as inputs an identification of the patient (1326), contact information of the patient (1328), and an identification of a restricted pharmaceutical associated with the electronic prescription (1330).

The system combines, via a processor, the first public key and the second public key sequentially, to form a combined public key (1332) and executes, via the processor, a hash function on the combined public key (1334). This combined public key is then transmitted to a pharmacy (1336).

In some configurations, the first algorithmic transformation further includes digital currency information for the medical professional. Likewise, the second algorithmic transformation can further include digital currency information for the patient.

In various configurations and embodiments, the execution of the hash function can further include encrypting the combined public key.

The combined public key can further include instructions regarding delivery to a home address of the patient. The blockchain system can be configured to allow the combined public key to be used only once with the electronic prescription. In other configurations, such as a recurring prescription, the combined public key can be used for a limited number of times, or limited within a predetermined period of time.

In some configurations, the method can further include transmitting the combined public key to a delivery drone associated with the pharmacy.

With reference to FIG. 14, an exemplary system includes a general-purpose computing device 1400, including a processing unit (CPU or processor) 1420 and a system bus 1410 that couples various system components including the system memory 1430 such as read-only memory (ROM) 1440 and random access memory (RAM) 1450 to the processor 1420. The system 1400 can include a cache of high-speed memory connected directly with, in close proximity to, or integrated as part of the processor 1420. The system 1400 copies data from the memory 1430 and/or the storage device 1460 to the cache for quick access by the processor 1420. In this way, the cache provides a performance boost that avoids processor 1420 delays while waiting for data. These and other modules can control or be configured to control the processor 1420 to perform various actions. Other system memory 1430 may be available for use as well. The memory 1430 can include multiple different types of memory with different performance characteristics. It can be appreciated that the disclosure may operate on a computing device 1400 with more than one processor 1420 or on a group or cluster of computing devices networked together to provide greater processing capability. The processor 1420 can include any general purpose processor and a hardware module or software module, such as module 1 1462, module 2 1464, and module 3 1466 stored in storage device 1460, configured to control the processor 1420 as well as a special-purpose processor where software instructions are incorporated into the actual processor design. The processor 1420 may essentially be a completely self-contained computing system, containing multiple cores or processors, a bus, memory controller, cache, etc. A multi-core processor may be symmetric or asymmetric.

The system bus 1410 may be any of several types of bus structures including a memory bus or memory controller, a peripheral bus, and a local bus using any of a variety of bus architectures. A basic input/output (BIOS) stored in ROM 1440 or the like, may provide the basic routine that helps to transfer information between elements within the computing device 1400, such as during start-up. The computing device 1400 further includes storage devices 1460 such as a hard disk drive, a magnetic disk drive, an optical disk drive, tape drive or the like. The storage device 1460 can include software modules 1462, 1464, 1466 for controlling the processor 1420. Other hardware or software modules are contemplated. The storage device 1460 is connected to the system bus 1410 by a drive interface. The drives and the associated computer-readable storage media provide non-volatile storage of computer-readable instructions, data structures, program modules and other data for the computing device 1400. In one aspect, a hardware module that performs a particular function includes the software component stored in a tangible computer-readable storage medium in connection with the necessary hardware components, such as the processor 1420, bus 1410, display 1470, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 1400 is a small, handheld computing device, a desktop computer, or a computer server.

Although the exemplary embodiment described herein employs the hard disk 1460, other types of computer-readable media which can store data that are accessible by a computer, such as magnetic cassettes, flash memory cards, digital versatile disks, cartridges, random access memories (RAMs) 1450, and read-only memory (ROM) 1440, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 1400, an input device 1490 represents any number of input mechanisms, such as a microphone for speech, a touch-sensitive screen for gesture or graphical input, keyboard, mouse, motion input, speech and so forth. An output device 1470 can also be one or more of a number of output mechanisms known to those of skill in the art. In some instances, multimodal systems enable a user to provide multiple types of input to communicate with the computing device 1400. The communications interface 1480 generally governs and manages the user input and system output. There is no restriction on operating on any particular hardware arrangement and therefore the basic features here may easily be substituted for improved hardware or firmware arrangements as they are developed.

The steps, aspects, and components outlined herein are exemplary and can be implemented in any combination thereof, including combinations that exclude, add, or modify certain steps, aspects, and/or components.

Use of language such as "at least one of X, Y, and Z" or "at least one or more of X, Y, or Z" are intended to convey a single item (just X, or just Y, or just Z) or multiple items (i.e., {X and Y}, {Y and Z}, or {X, Y, and Z}). "At least one of" is not intended to convey a requirement that each possible item must be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

We claim:

1. A method comprising:
   receiving, from an issuer, an electronic prescription for a patient;
   receiving a first public key associated with the issuer, the first public key:
      being associated with a blockchain;
      forming a first alphanumeric code; and
      being formed via a first algorithmic transformation, executed using a first private key associated with the issuer, of:
         an identification of the issuer;
         contact information of the issuer; and
         an identification of a restricted pharmaceutical associated with the electronic prescription;
   receiving a second public key associated with the patient, the second public key:
      being associated with the blockchain;
      forming a second alphanumeric code; and
      being formed via a second algorithmic transformation, executed using a second private key associated with the patient, of:
         an identification of the patient;
         contact information of the patient; and
         the identification of the restricted pharmaceutical associated with the electronic prescription;
   generating, via processor, a combined public key by combining, via the processor, the first public key and the second public key sequentially, the combined public key including at least one or more portions of the first public key and at least one or more portions of the second public key;
   generating, via the processor, a hash value by executing, via the processor, a hash function on: information regarding the restricted pharmaceutical associated with the electronic prescription, information regarding at least one additional product not associated with the electronic prescription, and the combined public key; and
   transmitting, via the processor, at least the hash value to a pharmacy, wherein the hash value is added to the blockchain.

2. The method of claim 1, wherein the first algorithmic transformation further includes digital currency information for the issuer.

3. The method of claim 2, wherein the second algorithmic transformation further includes digital currency information for the patient.

4. The method of claim 1, wherein execution of the hash function further comprises encrypting the combined public key.

5. The method of claim 1, wherein the combined public key further includes instructions regarding delivery to a home address of the patient.

6. The method of claim 1, wherein the blockchain allows the combined public key to be used only once with the electronic prescription.

7. The method of claim 1, further comprising:
   transmitting the combined public key to a delivery drone associated with the pharmacy.

8. A system comprising:
   a processor; and
   a computer-readable storage medium having instructions stored which, when executed by the processor, cause the processor to perform operations comprising:
      receiving, from an issuer, an electronic prescription for a patient;
      receiving a first public key associated with the issuer, the first public key:
         being associated with a blockchain;
         forming a first alphanumeric code; and
         being formed via a first algorithmic transformation, executed using a first private key associated with the issuer, of:
            an identification of the issuer;
            contact information of the issuer; and
            an identification of a restricted pharmaceutical associated with the electronic prescription;

receiving a second public key associated with the patient, the second public key being associated with the blockchain;

forming a second alphanumeric code; and being formed via a second algorithmic transformation, executed using a second private key associated with the patient, of:
- an identification of the patient;
- contact information of the patient; and
- the identification of the restricted pharmaceutical associated with the electronic prescription;

generating a combined public key by combining the first public key and the second public key sequentially, the combined public key including at least one or more portions of the first public key and at least one or more portions of the second public key;

generating a hash value by executing a hash function on: information regarding the restricted pharmaceutical associated with the electronic prescription, information regarding at least one additional product not associated with the electronic prescription, and the combined public key; and transmitting at least the hash value to a pharmacy, wherein the hash value is added to the blockchain.

9. The system of claim 8, wherein the first algorithmic transformation further includes digital currency information for the issuer.

10. The system of claim 9, wherein the second algorithmic transformation further includes digital currency information for the patient.

11. The system of claim 8, wherein execution of the hash function further comprises encrypting the combined public key.

12. The system of claim 8, wherein the combined public key further includes instructions regarding delivery to a home address of the patient.

13. The system of claim 8, wherein the blockchain allows the combined public key to be used only once with the electronic prescription.

14. The system of claim 8, the computer-readable storage medium having additional instructions stored which, when executed by the processor, cause the processor to perform operations comprising:

transmitting the combined public key to a delivery drone associated with the pharmacy.

15. A non-transitory computer-readable storage medium having instructions stored which, when executed by a computing device, cause the computing device to perform operations comprising:

receiving, from an issuer, an electronic prescription for a patient;

receiving a first public key associated with the issuer, the first public key:
- being associated with a blockchain;
- forming a first alphanumeric code; and
- being formed via a first algorithmic transformation, executed using a first private key associated with the issuer, of:
  - an identification of the issuer;
  - contact information of the issuer; and
  - an identification of a restricted pharmaceutical associated with the electronic prescription;

receiving a second public key associated with the patient, the second public key:
- being associated with the blockchain;
- forming a second alphanumeric code; and
- being formed via a second algorithmic transformation, executed using a second private key associated with the patient, of:
  - an identification of the patient;
  - contact information of the patient; and
  - the identification of the restricted pharmaceutical associated with the electronic prescription;

generating a combined public key by combining the first public key and the second public key sequentially, the combined public key including at least one or more portions of the first public key and at least one or more portions of the second public key;

generating a hash value by executing a hash function on: information regarding the restricted pharmaceutical associated with the electronic prescription, information regarding at least one additional product not associated with the electronic prescription, and the combined public key; and transmitting at least the hash value to a pharmacy, wherein the hash value is added to the blockchain.

16. The non-transitory computer-readable storage medium of claim 15, wherein the first algorithmic transformation further includes digital currency information for the issuer.

17. The non-transitory computer-readable storage medium of claim 16, wherein the second algorithmic transformation further includes digital currency information for the patient.

18. The non-transitory computer-readable storage medium of claim 15, wherein execution of the hash function further comprises encrypting the combined public key.

19. The non-transitory computer-readable storage medium of claim 15, wherein the combined public key further includes instructions regarding delivery to a home address of the patient.

20. The non-transitory computer-readable storage medium of claim 15, wherein the blockchain allows the combined public key to be used only once with the electronic prescription.

* * * * *